United States Patent [19]

Ohi et al.

[11] Patent Number: 5,728,692
[45] Date of Patent: Mar. 17, 1998

[54] METHOTREXATE DERIVATIVE

[75] Inventors: Nobuhiro Ohi, Shizuoka; Hiroshi Suzuki, Tokyo, both of Japan

[73] Assignee: Chugai Seiyaku Kabushiki Kaisha, Tokyo, Japan

[21] Appl. No.: 454,290

[22] PCT Filed: Dec. 24, 1995

[86] PCT No.: PCT/JP93/01867

§ 371 Date: Jun. 15, 1995

§ 102(e) Date: Jun. 15, 1995

[87] PCT Pub. No.: WO94/14810

PCT Pub. Date: Jul. 7, 1994

[30] Foreign Application Priority Data

Dec. 25, 1992 [JP] Japan ................................. 4-362027

[51] Int. Cl.$^6$ ...................... A61K 31/54; C07D 279/16
[52] U.S. Cl. ........................................ 514/224.2; 544/52
[58] Field of Search .......................... 514/224.2; 544/52

[56] References Cited

FOREIGN PATENT DOCUMENTS

| | | |
|---|---|---|
| 0 543 997 | 6/1993 | European Pat. Off. . |
| 0 632038 | 1/1995 | European Pat. Off. . |
| 93/15077 | 8/1993 | WIPO . |

OTHER PUBLICATIONS

Marpat Abstract of WO/92/3436 (Mar. 5, 1992) Ohi et al. (Abstract #117:48228).

*Primary Examiner*—Raymond Henley, III
*Attorney, Agent, or Firm*—Browdy and Neimark

[57] ABSTRACT

A compound represented by the general formula:

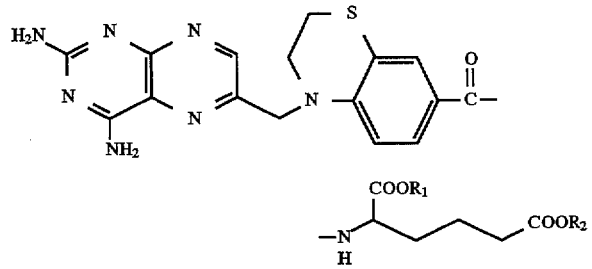

wherein $R_1$ and $R_2$, which may be the same or different, each represents a hydrogen atom or a lower alkyl group having from 1 to 4 carbon atoms and a salt thereof, and an antirheumatic agent containing, as an active ingredient, at least one of these compounds.

4 Claims, 1 Drawing Sheet

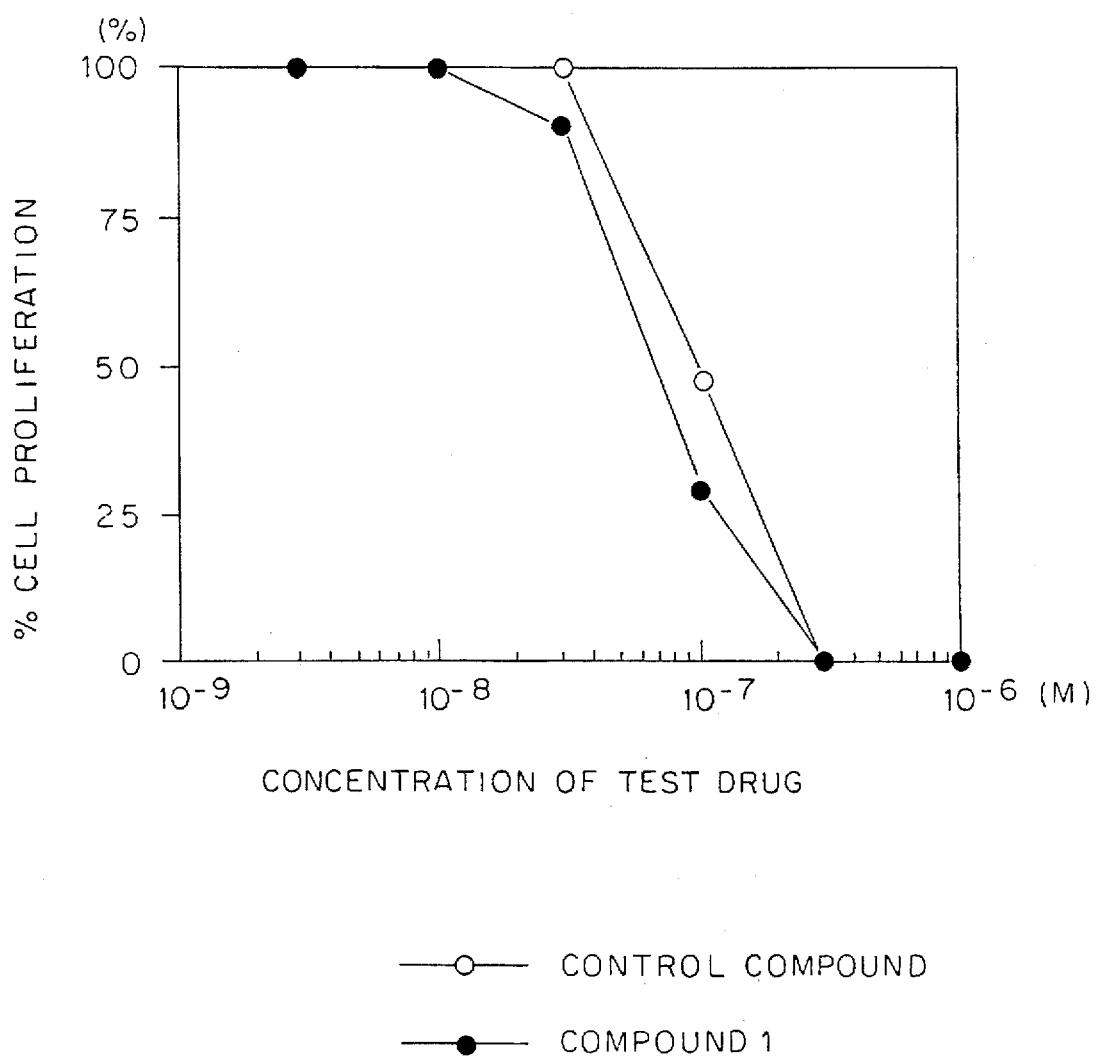

METHOTREXATE DERIVATIVE

This is a 371 of PCT/JP 93/01867 filed Dec. 24, 1993.

TECHNICAL FIELD

This invention relates to a novel methotrexate derivative, and, more specifically, to a novel methotrexate derivative useful as an antirheumatic agent.

TECHNICAL BACKGROUND

Hitherto, methotrexate has been used for many years as a treating agent for leukemia, but, since Gubner et al reported in 1951 the effectiveness by using aminopterin for rheumatoid arthritis (RA) and psoriasis, an attention has been drawn to aminopterin as a treating agent for RA and it has mainly been used in Europe and U.S.A. In relatively recent years, the method of use and the dosage thereof have been studied in more detail, and it becomes apparent that the treatment at a low dose of methotrexate exhibits low side effects and excellent effectiveness. However, since side effects such as hepatic disorders and lung fibrosis caused by administration of methotrexate is not negligible, development of a drug having less side effects and yet having excellent effects is desired.

Hitherto, methotrexate derivatives in which an alkyl group other than a methyl group has been introduced into $N^{10}$, for example, having the following formula:

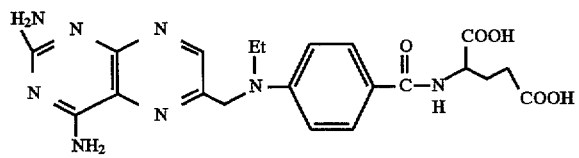

(J. Med. Chem., 22, 862 (1979) and having the following formula:

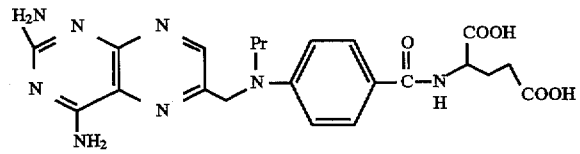

(J. Med. Chem., 25, 877 (1982) have been known, but none of these compounds showed a satisfactory activity.

The present inventors made extensive studies for developing compounds having a good balance between a pharmacological effect as an antirheumatic agent and side effects in the above type of methotrexate derivatives, and as a result completed the present invention.

DISCLOSURE OF THE INVENTION

The present invention relates to a methotrexate derivative represented by the following general formula (I):

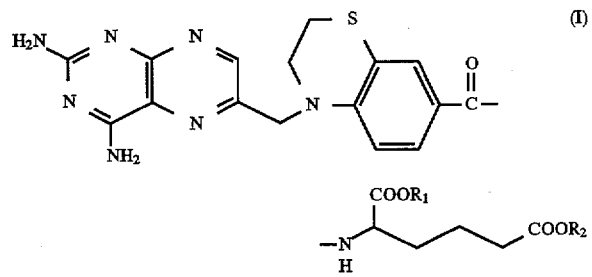

wherein $R_1$ and $R_2$ may be the same or different and each represents a hydrogen atom or a lower alkyl group having from 1 to 4 carbon atoms, and a salt thereof. Further, the present invention provides an antirheumatic agent containing at least one of these compounds as an effective ingredient.

BRIEF DESCRIPTION OF DRAWING

FIG. 1 shows a percent cell propagation at each of the concentrations of the test drugs.

BEST MODE FOR WORKING THE INVENTION

The compounds according to the present invention are described as a general formula in broad concept in WO 92/3436, but are novel compounds, none of which has been actually produced and have not been disclosed in literature references. These compounds are synthesized, for example, in the following manner:

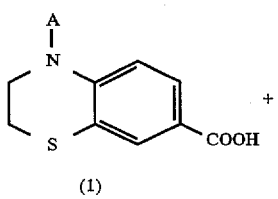

(1)

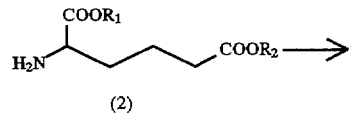

(2)

-continued

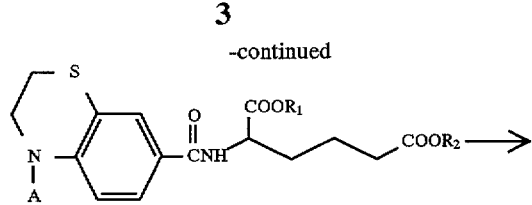
(3)

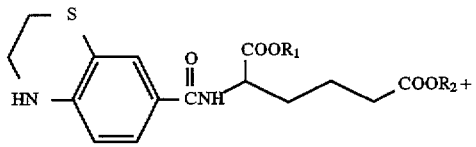
(4)

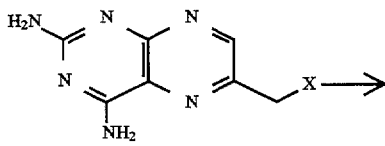
(5)

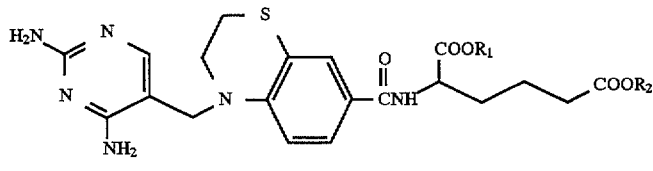
(6)

wherein $R_1$ and $R_2$ may be the same or different and each represents a hydrogen atom or a lower alkyl group having from 1 to 4 carbon atom, A represents a protective group, and X represents a halogen atom.

The reaction for obtaining a compound of the general formula (3) from a compound of the general formula (1) and a compound of the general formula (2) is performed by an amido-bond forming reaction generally used. For example, the compound of the general formula (1) is suspended in an acid halogenating agent such as thionyl chloride and oxalyl chloride and stirred in the presence of a catalytic amount of dimethylformamide, etc. at room temperature to obtain an acid halide which is then dissolved in a solvent such as dichloromethane and added to an aqueous solution of the compound of the general formula (2) under ice cooling or water cooling, followed by stirring at room temperature in the presence of an inorganic salt such as potassium carbonate, sodium hydroxide and sodium bicarbonate.

Examples of the protective group represented by A in the formula include a protective group for an amino group such as an acyl group, and preferably, a carbobenzoxy group, a tosyl group and an acetyl group. The compound of the general formula (1) can be obtained, for example, by the method described in International Publication WO 92/3436.

The compound of the general formula (3) is de-protected by the usual method thereby converting into the compound of the general formula (4). For example, when the protective group is a carbobenzoxy group or a tosyl group, removal of the protective group is achieved by adding the compound of the general formula (3) to a solution of anisole or phenol dissolved in a hydrogen bromide-acetic acid solution, followed by stirring at from 10° C. to 60° C., preferably at room temperature. Also, when the protective group is a carbobenzoxy group, removal of the protective group may be conducted by dissolving the compound of the general formula (3) in a solvent such as methanol, ethanol or acetic acid, and, after adding palladium-carbon thereto, the mixture is stirred in a hydrogen atmosphere at room temperature.

The reaction for obtaining the compound of the general formula (6) from the compound of the general formula (4) and the compound of the general formula (5) is carried out by stirring the compound of the general formula (4) and the compound of the general formula (5) in a solvent such as dimethylacetamide or dimethylformamide at from 0° C. to 100° C., preferably from 50° C. to 70° C. In particular, when $R_1$ and $R_2$ are hydrogen atoms, an aqueous alkali solution such as 1N aqueous solution of sodium hydroxide is added to a solvent such as methanol or ethanol, and the stirring is conducted at from 15° C. to 35° C. to obtain the object compound. Examples of the halogen atom represented by X in the formula include a bromine atom and a chlorine atom.

The compound of the present invention can also be synthesized by the following process:

(5)

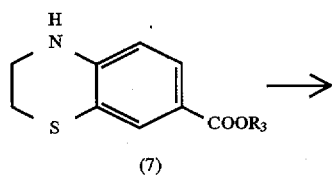

(7)

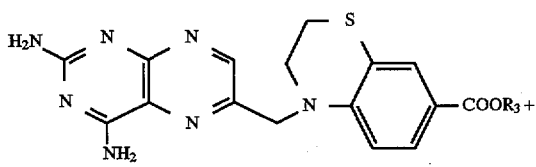

(8)

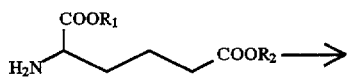

(2)

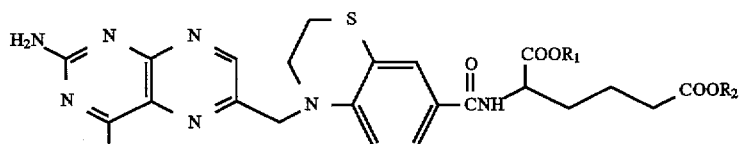

(6)

wherein $R_1$, $R_2$ and $R_3$ may be the same or different and each represents a hydrogen atom or a lower alkyl group having from 1 to 4 carbon atoms, and X represents a halogen atom.

The reaction for obtaining the compound of the general formula (8) from the compound of the general formula (5) and the compound of the general formula (7) is carried out in the same manner as described for obtaining the compound of the general formula (6) from the compound of the general formula (4) and the compound of the general formula (5). The compound of the general formula (7) can be obtained, for example, by the process described in International Publication WO 92/3436.

The reaction for obtaining the compound of the general formula (6) from the compound of the general formula (8) and the compound of the general formula (2) is carried out by the amido-bond forming reaction generally used.

The compound of the present invention can also be obtained as a salt thereof by the usual method. The salt which can be used include, for example, an inorganic acid salt such as hydrochloride, hydrobromide, hydroiodide, sulfate and phosphate, an organic acid salt such as succinate, malonate, acetate, maleate, fumarate, oxalate, gluconate, mandelate, benzoate, salicylate, methane-sulfonate, benzenesulfonate and p-toluenesulfonate, and a metal salt such as a sodium salt, a potassium salt and a magnesium salt, and preferably an inorganic salt and an organic salt, and more preferably hydrobromide or methanesulfonate.

The pharmaceutical agent containing the compound of the present invention can be administered orally or parenterally, but the oral administration or a topical administration such as intra-articular is preferred. The dose to be administered varies depending upon the body weight and the conditions of disease of patients, but is generally preferably at from 0.01 to 100 mg/day/person.

The form of the pharmaceutical agent containing the compound of the present invention include a liquid preparation such as injection, tablet, capsule, powder, etc.

The compounds represented by the general formula (I) according to the present invention are excellent in the balance between the antirheumatic activity and the toxicity as compared with methotrexate and the existing methotrexate derivatives and, therefore, are useful as antirheumatic agents.

EXAMPLES

The compounds of the present invention are further illustrated in more detail with reference to examples thereof, but the present invention is not limited by these examples.

Reference Example 1

Synthesis of Dimethyl N-(4-carbobenzoxy-3,4-dihydro-2H-1,4-benzothiazine-7-carbonyl)-L-α-aminoadipate Thionyl chloride (10 ml) was added to 4-carbobenzoxy-3,4-dihydro-2H-1,4-benzothiazine-7-carboxylic acid (2.0 g), followed by stirring at room temperature for 2 hours. Then, the reaction solution was concentrated under reduced pressure to dryness. The resulting solid material was dissolved in dichloromethane (25 ml), and to the resulting solution were added subsequently an aqueous solution (25 ml) of dimethyl L-α-aminoadipate hydrochloride (1.4 g) and then potassium carbonate (3.4 g), followed by stirring overnight. The reaction mixture was poured into a saturated aqueous solution of sodium bicarbonate, and an organic substance was extracted with chloroform. Further, the chloroform layer was washed with 1N hydrochloric acid, dried over sodium sulfate, and the solvent was distilled off under reduced pressure. The resulting residue was subjected to silica gel column chromatography using chloroform:methanol=100:1 as an eluting solvent to obtain the titled compound (2.35 g).

$^1$H NMR (CDCl$_3$, δ values): 1.6–2.1 (4H,m), 2.37 (2H, t,J=7.1 Hz), 3.20 (2H,m), 3.67 (3H, s), 3.78 (3H, s), 3.98 (2H,m), 4.77 (1H,m), 5.23 (2H, s), 6.75 (1H, d,J=7.3 Hz), 7.36 (5H,m), 7.48 (2H,m), 7.63 (1H,d,J=2.5 Hz)

Reference Example 2

Synthesis of Dimethyl N-(3,4-dihydro-2H-1,4-benzothiazine-7-carbonyl)-L-α-aminoadipate The compound (14.8 g) of Reference Example 1 was added to a 30% hydrogen bromide-acetic acid solution (200 ml) of amisole (15 g), followed by stirring at room temperature for 4 hours. Then, a large amount of ether was added to the reaction mixture whereby a red brown oily substance was precipitated. Most of the ethereal layer was removed and the oily substance was suspended in chloroform. The resulting suspension was washed with a saturated aqueous solution of sodium bicarbonate and extracted with chloroform. The chloroform layer was dried over sodium sulfate, and the solvent was distilled off under reduced pressure to obtain the titled compound (7.6 g).

$^1$H NMR (CDCl$_3$-CD$_3$OD, δ values): 1.6–2.0 (4H,m), 2.40 (2H,t,J=6.8 Hz), 3.01 (2H,m), 3.68 (5H,m), 3.78 (3H, s), 4.65 (1H,m), 6.50 (1H, d,J=8.8 Hz), 7.41 (2H,m), 7.51 (1H, d,J=2.0 Hz)

Example 1

Synthesis of Dimethyl N-(1-((2,4-diamino-6-pteridinyl)methyl)-3,4-dihydro-2H-1,4-benzothiazine-7-carbonyl)-L-α-aminoadipate The compound (7.6 g) of Reference Example 2 and a 6-bromomethyl-2,4-diaminopteridine hydrobromide salt isopropanol adduct (8.2 g) were suspended in dimethylacetamide (120 ml), followed by stirring at 60° C. for 13 hours. After cooling, the reaction mixture was poured into a saturated aqueous solution of sodium bicarbonate, and the mixture was extracted with a mixed solvent of chloroform:methanol=10:1. The organic layer was dried over sodium sulfate, and then the solvent was distilled off under reduced pressure. The resulting residue was subjected to silica gel column chromatography using chloroform:methanol=10:1 as an eluting solvent to obtain the titled compound (5.8 g).

$^1$H NMR (CDCl$_3$-CD$_3$OD, δ values): 1.6–2.0 (4H,m), 2.39 (2H,t,J=7.1 Hz), 3.17 (2H,m), 3.68 (3H, s), 3.76 (3H, s), 3.94 (2H,m), 4.66 (1H,m), 4.79 (2H, s), 6.70 (1H,d,J=8.8 Hz), 7.42 (2H,m), 7.62 (1H,d,J=2.4 Hz), 8.67 (1H, s)

Example 2

Synthesis of N-(1-((2,4-diamino-6-pteridinyl)methyl)-3,4-dihydro-2H-1,4-benzothiazine-7-carbonyl)-L-α-aminoadipic Acid The compound (5.8 g) of Example 1 was dissolved in ethanol (300 ml), and 1N aqueous solution of sodium hydroxide (32.2 ml) was added thereto at 35° C., followed by stirring at room temperature overnight. Then, the reaction solution was evaporated under reduced pressure to dryness. The resulting solid substance was dissolved in water (100 ml), and the solution was adjusted to a pH of 3.7 with 1N hydrochloric acid, followed by allowing to stand in a cool place for 2 hours. The precipitate formed was separated by filtration to obtain the titled compound (4.5 g).

$^1$H NMR (DMSO-d$_6$ δ values): 1.5–1.9 (4H,m), 2.21 (2H,t,J=7.1 Hz), 3.15 (2H,m), 3.96 (2H,m), 4.30 (1H,m), 4.76 (2H, s), 6.78 (1H,d,J=8.8 Hz), 7.44 (1H,m), 7.60 (1H, s), 8.17 (1H,d,J=7.8 Hz), 8.65 (1H, s)

Example 3

Synthesis of N-(1-((2,4-diamino-6-pteridinyl)methyl)-3,4-dihydro-2H-1,4-benzothiazine-7-carbonyl)-L-α-aminoadipic Acid Hydrobromide (⅔ Hydrate)

The compound (100 mg) obtained in Example 2 was suspended in hydrobromic acid (10 ml) and dissolved by warming up to 60° C. in a water bath. Then, the solution was filtered through a cotton plug, and the filtrate was cooled to room temperature, followed by allowing to stand overnight. The precipitated needle crystals were separated by filtration and dried while heating in vacuum to obtain the titled compound (92 mg).

$^1$H NMR (DMSO-d$_6$, δ values): 1.42–1.90 (4H,m), 2.21 (2H, t,J=7.3 Hz), 3.19 (2H,m), 3.97 (2H,m), 4.26 (1H,m), 4.84 (2H, s), 6.76 (1H,d,J=8.9 Hz), 7.44 (1H, dd, J=2.3 Hz,8.8 Hz), 7.62 (1H,d,J=1.97 Hz), 8.23 (1H, d,J=8.2 Hz), 8.80 (1H, s)

Elementary Analysis C:43.76, H:4.31, N:18.73, S:5.12, Br:13.43 Calc'd Values C:43.73, H:4.37, N:18.54, S:5.31, Br:13.22

Empirical Formula $C_{22}H_{24}N_8O_5S \cdot HBr \cdot 2/3H_2O$

Test Example 2.5×10$^3$ synovial cells from RA patient were cultured (in 96-well culture plate) with various concentrations of a test compound. Three days later, 1 μCi $^3$H-UdR was added to each well and cultured for further 2 days. After culture, intracellular uptake of $^3$H-UdR was measured by a scintillation counter.

The drugs used for the test were as follows:

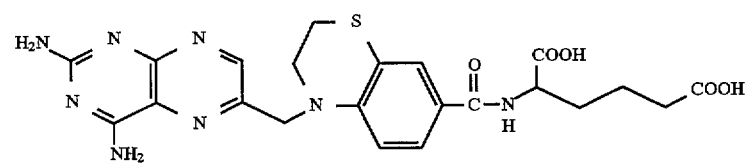

Compound 1

-continued

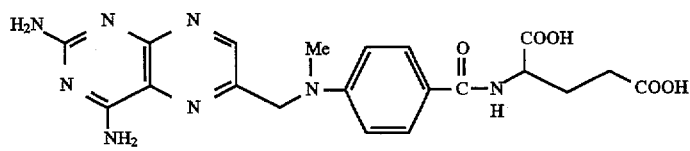

The results are shown in FIG. 1. As is apparent from FIG. 1, the compound of the present invention was confirmed to have a more excellent inhibitory activity to synovial cell proliferation than the control compound.

Possibility of Utilization in Industry

The compounds represented by the general formula (I) according to the present invention have excellent antirheumatic activity and are useful as antirheumatic agents in view of their low toxicity as compared to methotrexate.

I claim:

1. A compound represented by the general formula (I):

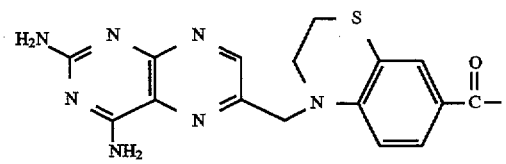

Control Compound

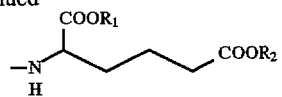

-continued $$\begin{array}{c} COOR_1 \\ | \\ -N-\phantom{xxx}COOR_2 \\ | \\ H \end{array}$$

wherein $R_1$ and $R_2$, which may be the same or different, each represents a hydrogen atom or a lower alkyl group having from 1 to 4 carbon atoms, or a salt thereof.

2. A compound according to claim 1 wherein at least one of $R^1$ and $R^2$ is hydrogen.

3. A compound according to claim 1 wherein both $R^1$ and $R^2$ are H.

4. Antirheumatic agent containing composition comprising, as an active ingredient, an antirheumatic-effective amount of at least one of the compounds represented by the general formula (I) as defined in claim 1 and the salts thereof, and a pharmaceutical excipient.

* * * * *

UNITED STATES PATENT AND TRADEMARK OFFICE
CERTIFICATE OF CORRECTION

PATENT NO. : 5,728,692
DATED : Mar. 17, 1998
INVENTOR(S) : Nobuhiro OHI et al.

It is certified that error appears in the above-identified patent and that said Letters Patent is hereby corrected as shown below:

Cover page, item [22], the PCT filing date, delete "1995" and insert therefor --1993--.

Signed and Sealed this

Twentieth Day of October, 1998

Attest:

BRUCE LEHMAN

Attesting Officer

Commissioner of Patents and Trademarks